(12) United States Patent
Mostert

(10) Patent No.: US 10,457,633 B2
(45) Date of Patent: Oct. 29, 2019

(54) UREA PRODUCTION WITH CONTROLLED BIURET

(71) Applicant: STAMICARBON B.V., Sittard (NL)

(72) Inventor: Eelco Mostert, Sittard (NL)

(73) Assignee: STAMICARBON B.V., Sittard (NL)

( * ) Notice: Subject to any disclaimer, the term of this patent is extended or adjusted under 35 U.S.C. 154(b) by 0 days.

(21) Appl. No.: 15/735,153

(22) PCT Filed: Apr. 28, 2017

(86) PCT No.: PCT/NL2017/050271
§ 371 (c)(1),
(2) Date: Dec. 8, 2017

(87) PCT Pub. No.: WO2017/192032
PCT Pub. Date: Nov. 9, 2017

(65) Prior Publication Data
US 2019/0210963 A1    Jul. 11, 2019

(30) Foreign Application Priority Data
May 3, 2016  (EP) .................................... 16168115

(51) Int. Cl.
*C07C 273/04*  (2006.01)
*C07C 273/16*  (2006.01)

(52) U.S. Cl.
CPC .......... *C07C 273/04* (2013.01); *C07C 273/16* (2013.01)

(58) Field of Classification Search
None
See application file for complete search history.

(56) References Cited

U.S. PATENT DOCUMENTS 2,916,516 A * 12/1959 Michclitsch .......... C07C 273/16
                                                    159/15
3,147,174 A *  9/1964 Cook ..................... C05C 9/005
                                                    159/13.2
3,151,156 A *  9/1964 Marten ................... C05C 9/005
                                                    564/73

(Continued)

FOREIGN PATENT DOCUMENTS

GB            959358         6/1964

OTHER PUBLICATIONS

Meessen ("Urea" Ullmann's Encyclopedia of Industrial Chemistry, 2010, p. 657-695) (Year: 2010).*

(Continued)

*Primary Examiner* — Amy C Bonaparte
(74) *Attorney, Agent, or Firm* — Morrison & Foerster LLP

(57) ABSTRACT

Disclosed is a novel method of controlling the formation of biuret in urea production. This is accomplished by reducing or preventing the formation of biuret in a concentration section, particularly in one or more concentrators or evaporators. The method comprises controlling the residence time of a urea aqueous stream treated in such concentration section in a manner independently of the volume flow per time interval of said stream into said concentration section. The residence time can be controlled, e.g., by providing the concentration section with an adjustable volume or by adding a gas to the urea stream to be treated. A combination of such measures can also be applied.

9 Claims, 1 Drawing Sheet

(56) References Cited

U.S. PATENT DOCUMENTS

| | | | | |
|---|---|---|---|---|
| 3,171,770 A | * | 3/1965 | Biekart | C07C 273/16 |
| | | | | 159/47.2 |
| 3,184,508 A | * | 5/1965 | Kaasenbrood | C07C 273/16 |
| | | | | 564/38 |
| 3,211,788 A | * | 10/1965 | Cook | C07C 273/16 |
| | | | | 564/73 |
| 3,223,145 A | | 12/1965 | Templeton et al. | |
| 3,287,407 A | * | 11/1966 | Zardi | C07C 273/16 |
| | | | | 564/73 |
| 3,491,821 A | * | 1/1970 | Graumann | B01D 1/065 |
| | | | | 159/13.4 |
| 3,903,158 A | | 9/1975 | Fuentes et al. | |
| 4,316,767 A | * | 2/1982 | Saida | C07C 273/16 |
| | | | | 159/13.2 |
| 4,345,099 A | * | 8/1982 | Young | C07C 275/62 |
| | | | | 504/328 |
| 4,866,207 A | * | 9/1989 | Jonckers | B01D 1/065 |
| | | | | 564/73 |
| 5,273,623 A | * | 12/1993 | Granelli | B01D 3/38 |
| | | | | 159/31 |
| 2014/0206902 A1 | * | 7/2014 | Mennen | C07C 273/04 |
| | | | | 564/67 |

OTHER PUBLICATIONS

International Search Report and Written Opinion for PCT/NL2017/050271, dated Aug. 23, 2017, 12 pages.

\* cited by examiner

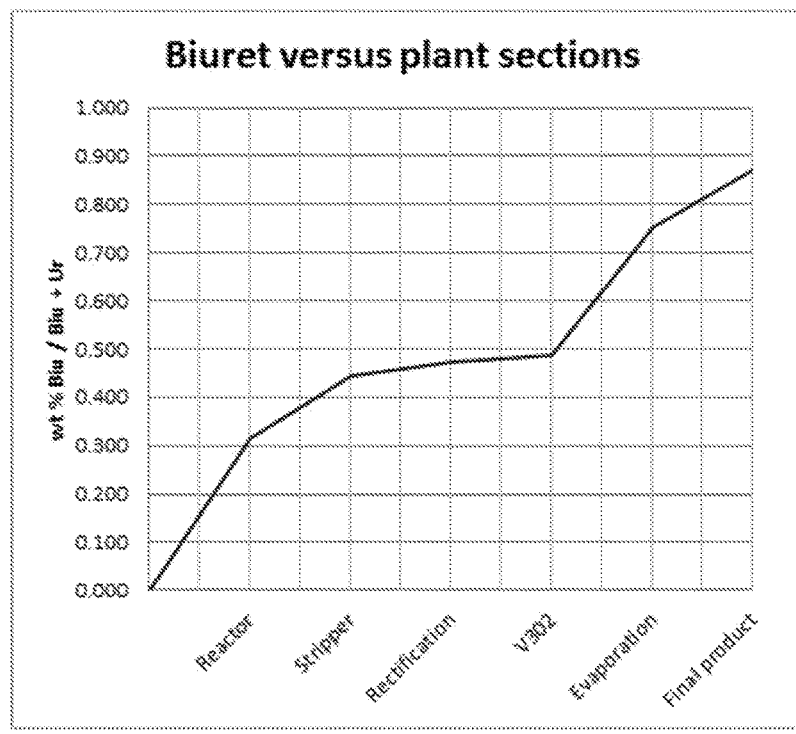

UREA PRODUCTION WITH CONTROLLED BIURET

CROSS-REFERENCE TO RELATED APPLICATIONS

This application is the national phase of PCT application PCT/NL2017/050271 having an international filing date of 28 Apr. 2017, which claims benefit of European patent application No. 16168115.0 filed 3 May 2016. The contents of the above patent applications are incorporated by reference herein in their entirety.

FIELD OF THE INVENTION

The invention is in the field of urea production, and pertains to controlling the amount of biuret produced as a by-product. The invention particularly pertains to controlling the amount of biuret in urea production plants that are operated at a reduced capacity. The invention relates to a process as well as a plant, and to modernization of pre-existing plants.

BACKGROUND OF THE INVENTION

Urea is generally produced from ammonia and carbon dioxide. It can be prepared by introducing an ammonia excess together with carbon dioxide at a pressure between 12 and 40 MPa and at a temperature between 150° C. and 250° C. into a urea synthesis zone. The resulting urea formation can be presented best in the form of two consecutive reaction steps, in the first step ammonium carbamate being formed according to the exothermic reaction:

$2NH_3 + CO_2 \rightarrow H_2N\text{---}CO\text{---}ONH_4$ after which the ammonium carbamate formed is dehydrated in the second step to give urea according to the endothermic equilibrium reaction:

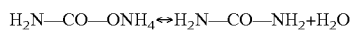

$H_2N\text{---}CO\text{---}ONH_4 \leftrightarrow H_2N\text{---}CO\text{---}NH_2 + H_2O$ The extent to which these reactions take place depends among other things on the temperature and the ammonia excess used. The reaction product obtained in a urea synthesis solution substantially consists of urea, water, unbound ammonia and ammonium carbamate. The ammonium carbamate and the ammonia are removed from the solution and are generally returned to the urea synthesis zone.

In addition to the above-mentioned solution in the urea synthesis zone, a gas mixture is formed which consists of unconverted ammonia and carbon dioxide together with inert gases, the so called reactor off-gas. The urea synthesis section may comprise separate zones for the formation of ammonium carbamate and urea. These zones may also be combined in a single apparatus.

Different urea production process exist. These processes, and by analogy the plants in which these processes are conducted, generally provide for the following stages: synthesis, recovery of unreacted starting materials, downstream processing, and finishing. Thereby synthesis and recovery sections are applied that are connected with each other so as to form a synthesis loop, whereby starting materials (ammonia and carbon dioxide, particularly in the form of ammonium carbamate) are recovered and recycled back to synthesis stage. The output of the synthesis loop is generally a purified aqueous urea stream, having a concentration of 50 wt. % urea or higher, generally up to 75-80 wt % before said stream is subjected to final concentration step(s).

The downstream processing generally refers to one or more sections, zones, or units in which the aforementioned aqueous urea stream is further concentrated. Such further concentration is typically conducted by evaporation, and the concentration section is frequently referred to as an evaporation section.

One of the challenges in urea production concerns controlling the amount of biuret formed as a by-product, and generally present in urea products such as prills or granules. Biuret is dimer of urea, and is formed under release of ammonia. The amount of biuret is an indicator of the urea quality as can be sold. Typically, a worldwide standard specification for biuret in urea products, is below 1 wt. %. E.g., for fertilizer purposes, the amount of biuret is generally below 0.9 wt. %. For other applications, such as the use of an aqueous urea solution in a unit for the reduction of NOx in diesel exhaust gases (particularly known as Diesel Exhaust Fluid, traded as AdBlue®), the biuret content is required to be still lower.

In urea plants operating on the basis of old, once-through technology the formation of biuret is not a significant problem. Modern plants, such as urea stripping plants, however tend to result in a higher amount of biuret formed. It remains desired to better control biuret production.

An additional problem is that it is more difficult to produce urea according to desired biuret specifications, in the event that the plant in which the urea is produced, is not operated on full capacity. Generally, biuret levels are guaranteed for a plant operating at full capacity. In practice, this means that manufacturers operating their plants at reduced capacity, run a risk that the products produced do not meet specifications for all end-uses. It would be desired to provide a urea manufacturing process, and a plant suitable for such process, that allows controlling biuret formation also in the event that the plant in which the urea is produced is operated at a reduced capacity.

GB959.358 discloses a process for producing urea prills of low biuret content according to which urea containing degasified reactor effluent is passed from the primary purification zone to a second purification zone wherein the effluent is heated under specified conditions of temperature and pressure. A highly concentrated biuret-containing melt of urea is withdrawn from the second purification zone. The biuret concentration of the urea withdrawn from that second purification zone is said to depend on the degree of concentration of the urea achieved. The biuret concentration is further reduced by contacting the urea melt with an ammonia containing gas at a temperature above the melting point of pure urea for a period of time sufficient to achieve equilibrium between the reacting ammonia and biuret and urea.

U.S. Pat. No. 3,223,145 discloses a method for preparing urea prills which are at the same time mechanically strong and dense, and have a low tendency to pick up water, buy controlling the overall urea heating time and temperature. As a feed, use is made of molten urea with a low water content and an excessive biuret content. Biuret contained in the molten urea is removed by carrying out dehydration of the molten urea as rapidly as possible, at as low a temperature as possible, or in other words by minimizing the time during which and the temperature to which dehydrated, molten urea is heated.

SUMMARY OF THE INVENTION

In order to better address one or more of the aforementioned desires, the invention provides, in one aspect, a process for producing urea, the process comprising a. subjecting ammonia and carbon dioxide to urea forming conditions in a urea synthesis section, thereby producing a urea aqueous stream;
b. sending the urea aqueous stream to a recovery section;
c. subjecting, in the recovery section, the urea aqueous stream to recovery of unreacted ammonia and carbon dioxide from said urea aqueous stream, thereby producing recovered ammonia and carbon dioxide, and a purified urea aqueous stream;
d. recycling said recovered ammonia and carbon dioxide to the synthesis section;
e. sending the purified urea aqueous stream to a concentration section;
f. subjecting, in the concentration section, the purified urea aqueous stream to removal of water, thereby producing a concentrated urea stream;
wherein the residence time of the purified urea aqueous stream in the concentration section is controlled independently of the volume flow per time interval of the purified urea aqueous stream into the concentration section.

In another aspect, the invention presents a plant for the production of urea, said plant comprising a urea synthesis section having an inlet for ammonia and carbon dioxide and an outlet for a urea aqueous solution, said outlet being in fluid communication with a recovery section having an inlet for the urea aqueous solution, an outlet for ammonia and carbon dioxide recycle, and an outlet for a purified urea aqueous stream, said outlet for ammonia and carbon dioxide recycle being in fluid communication with an inlet of the synthesis section, recovery section, said outlet for a purified urea aqueous stream being in fluid communication with an inlet of a concentration section; said concentration section having an outlet for steam or steam condensate, and an outlet for a concentrated urea stream, wherein the plant is configured such as to allow the residence time of the purified urea aqueous stream in the concentration section to be controlled independently of the volume flow per time interval of the purified urea aqueous stream into the concentration section.

In a still further aspect, the invention is a method of modernizing a pre-existing plant for the production of urea, said plant comprising a urea synthesis section having an inlet for ammonia and carbon dioxide and an outlet for a urea aqueous solution, said outlet being in fluid communication with a recovery section having an inlet for the urea aqueous solution, an outlet for ammonia and carbon dioxide recycle, and an outlet for a purified urea aqueous stream, said outlet for ammonia and carbon dioxide recycle being in fluid communication with an inlet of the synthesis section, recovery section, said outlet for a purified urea aqueous stream being in fluid communication with an inlet of a concentration section; said concentration section having an outlet for steam or steam condensate, and an outlet for a concentrated urea stream, the modernizing method comprising configuring the plant in such a way as to allow the residence time of the purified urea aqueous stream in the concentration section to be controlled independently of the volume flow per time interval of the purified urea aqueous stream into the concentration section.

DESCRIPTION OF THE DRAWING

FIG. 1 is a graph originating from the present inventors and representing the formation of biuret in the sections of a conventional urea stripping plant, when operated in a conventional manner. The sections are indicated on the X-axis, with the upstream side left and the downstream side right. The section "rectification" is in fact part of a recovery section. The section "V302" is a urea storage tank. The cumulative percentages of biuret formed are indicated on the X-axis as a percentage of biuret over the sum of urea and biuret. The graph indicates that, in addition to the conventional belief that biuret is mainly formed in the stripper, a substantial amount of the biuret is formed in the evaporation (i.e., concentration) section.

DETAILED DESCRIPTION OF THE INVENTION

The invention is based, in a general sense, on the judicious insight that a significant amount of biuret formation can be avoided by decoupling the amount of inflow of urea into a concentration section, from the residence time of the urea within said concentration section. Hitherto, controlling the formation of biuret has focused on events in the urea synthesis section. This is consistent with the general belief that most of the biuret is formed in the stripper. The inventors now believe, without wishing to be bound by theory, that a substantial part of biuret is produced as a result of an unequal distribution of the residence time of urea in the concentration section, which leads to corresponding variations in the residence time. This effect is particularly exhibited in the event of varying operational plant capacities.

In accordance with the invention, the above insight is put to use by controlling the residence time of urea in the concentration section independently of the volume flow per time interval of such urea into the concentration section. The volume flow per time interval can be indicated in, e.g., $m^3/s$ or $m^3/h$.

In conventional urea production processes, the concentration section will just receive a flow of urea, i.e., the aforementioned purified urea aqueous stream, the amount of which is given by the operational choices in the upstream process. The residence time of the urea in the concentration section, will be dependent on the flow of urea volume per time interval into said concentration section. Conventional concentrators do not have a provision allowing the residence time of urea stream entering it, to be independently controlled. Put simply, the higher said flow, the shorter the residence time in the concentration section will be.

This can be illustrated particularly with reference to a customary embodiment of a concentrator, which comprises one or more vertical tubes from which water is made to evaporate. In such a system, liquid will enter the evaporator tube from the bottom, and due to the heat input (such as by steam) at some point evaporation of the liquid will start and vapor bubbles will be formed. As a result of the flow of liquid into the tube, the level of liquid will be rising, with increasing formation of vapor bubbles. Ultimately, the vapor flow will become high enough for the resulting flow of vapor and liquid to be blown out the tube, with a generally high velocity, due to the increased amount of vapor. As a result of this process, the higher residence time is where the liquid flow enters, viz., at the bottom of the tube. At a reduced volume flow (which may be due to a reduced plant load), the residence time will increase, since it takes more time for the liquid to reach a state where it will be blown out of the tube, with vapor, as identified above.

The invention puts to use the recognition of the importance of residence time in a concentrator of a urea plant. In embodiments wherein the plant is a new plant, also referred to as a grassroots plant, this is realized by configuring the concentration section such as to allow the residence time of liquid (i.e., a purified urea aqueous stream) to be controlled independently of the volume flow per time interval of said liquid into the concentration section. In embodiments wherein the plant is a pre-existing urea production plant, the invention can be put to use by accordingly adapting the concentration section (which is normally present in a urea plant).

It is noted that a concentration section in a urea plant may contain a plurality of concentrators. Thereby, typically, in a sequence of two or more concentrators, the aqueous urea solution is brought to higher concentrations, and consequently to higher temperatures. Said sequence of concentrators, if placed in series, will have, at the upstream side a first cocentrator, and downstream thereof second and, optionally, further concentrators. In an interesting embodiment, the step according to the invention of controlling the residence time in the concentration section, is applied to one or more of the second or further concentrators. Thereby it is conceivable that said step is not applied to the first concentrator and/or, in the event of more than three concentrators, not to one or more of the first, second and further concentrators. Particularly, an interesting embodiment in the event of two or more subsequent concentrators, is to apply the step of controlling the residence time only to those concentrators wherein the aqueous urea stream is subjected to a temperature above 125° C., such as above 130° C.

In accordance with the invention, in all embodiments, the resulting plant will have a provision allowing the residence time in the concentration section to be controlled independently of the flow of liquid into said section. When in operation, a plant according to the invention will produce urea in a process that involves a step corresponding to employing the aforementioned provision.

The aforementioned provision will now be further explained with reference to the general set-up of a urea production plant. Such a plant will comprise at least the following sections: a urea synthesis section, a recovery section, and a concentration section. Typically, a urea production plant will also comprise a finishing section downstream of the concentration section, in which a urea melt obtained from the concentration section is converted into a final, solid product such as prills or granules. The foregoing sections are in such fluid communication as is known in the art, generally providing for a urea synthesis loop to which recovered ammonia and carbon dioxide (including ammonium carbamate) are recycled back.

The urea synthesis section comprises one or more inlets for a feed of reactants, viz. ammonia and carbon dioxide. In view of the necessary urea-forming conditions, the synthesis section will generally be operated under a high pressure (typically 12-40 MPa) and is customarily referred to as a HP (high pressure) section. The synthesis section usually comprises a reactor, and the inlets can be provided in the reactor. In many urea plants, the synthesis section also comprises other HP equipment, such as a stripper and a condenser. The stripper can be a thermal stripper (which operates on the basis of heat only), but more customarily is a stripper operating on the basis of a stripping gas (ammonia or, more commonly, carbon dioxide). The inlets for feed reactants into the synthesis section can also be comprised in such other equipment. E.g., a frequently used process is a carbon dioxide stripping processes, in which typically a carbon dioxide feed is applied as a stripping gas, and is made to enter the synthesis section via an inlet to the stripper.

The synthesis section has an outlet (i.e., a liquid outlet) for a urea aqueous solution (i.e., a urea synthesis solution resulting from subjecting ammonia and carbon dioxide to urea-forming conditions) that is in fluid communication with at least one recovery section (sometimes also referred to as a recirculation section). This generally comprises one or more sections operated at a pressure below 7 MPa. This can be a low pressure (LP) section, a medium pressure (MP) section, or both. LP generally is 0.1 to 1 MPa, MP is generally 1 to 7 MPa, more typically 1-5 MPa.

For completeness' sake, it is mentioned that the synthesis section will also comprise, e.g., at the reactor, a gas outlet for unreacted gaseous ammonia and carbon dioxide, which will generally be recycled back into the synthesis section. Also, in the event of a stripping process as mentioned above, the stripper will have a gas outlet for unreacted gaseous ammonia and/or carbon dioxide and, if applicable, also for utilized stripping gas).

The at least one recovery section has an inlet for the aforementioned urea aqueous solution resulting from synthesis. In the recovery section, unreacted ammonia and carbon dioxide are recovered, and recycled back to the synthesis section. The recovery section therefore comprises an outlet for ammonia and carbon dioxide recycle, which is in fluid communication with an inlet of the synthesis section. The recycle frequently takes the form of a LP ammonium carbamate stream, which is brought up to synthesis pressure prior to entering the synthesis section. The recovery section comprises an outlet for a urea aqueous solution, which is purified as a result of the ammonium carbamate recovery in the recovery section. Said outlet is in fluid communication with downstream sections, thereby (directly or indirectly) with an inlet of a concentration section. The concentration section serves to increase the urea concentration by removal of water. This is generally accomplished by evaporation, and the concentration section has an outlet for water, i.e., typically either a gas outlet for steam or a liquid outlet for steam condensate. The concentration section also comprises an outlet for the concentrated urea stream that results from the removal of water in the concentration section. The concentrated urea stream is often referred to as a urea melt which is suitable to be converted in a urea finishing section in a solid urea product. The urea melt typically has a urea concentration of greater than 90 wt %, preferably greater than 95 wt %, such as greater than 97 wt %.

In accordance with the invention, the provision allowing an independent control of the residence time of aqueous urea in the concentration section can be an additional unit. Such unit can be positioned upstream of the concentration section, and downstream of the recovery section. In this embodiment, such unit serves to collect a predetermined amount of urea before this is made to enter the concentration section. As a result, the fluctuations in the flow or urea from the upstream sections (e.g., in the event that the plant is operated at a reduced capacity) can be rectified. Whilst this may result in a batch-wise flow of urea into the concentration section, the operation of the latter section can be at normal speed.

In a preferred embodiment, the continuous flow of urea is preserved, by allowing a gas to enter the concentration section with the purified urea aqueous stream. This results in gas being added to said stream. The corresponding provision made to the plant, is a gas inlet into the concentration section, preferably at the same end or side of a liquid inlet, into the concentration section, for the purified aqueous urea solution.

The gas stream can be added further downstream in the concentration section. In particular, in the event that the concentration section is comprised of a plurality of concentrators, the gas inlet may be upstream of one of the concentrators or the gas inlet may be on one of the concentrators. In a preferred embodiment the gas is added directly upstream of, or into the last concentrator. Alternatively, the gas inlet is upstream of the concentration section, into any conduit or unit through which, in operation, the purified urea stream is allowed to flow between the recovery section and the concentration section.

The added gas can be any kind of gas, for example an inert gas such as air or nitrogen. The gas serves to fill the volume of the concentration section to a desired level. The gas takes up part of the volume of the concentrator, thereby effectively reducing the volume occupied by the purified urea aqueous stream. This serves to reduce the residence time of the urea aqueous stream in the concentration section. Preferably the gas is only partially soluble in the urea aqueous stream. Thereby the total amount the gas added is greater than the soluble amount. More preferably, the gas is substantially insoluble in the urea aqueous stream. The lower the solubility of the gas in the urea aqueous stream, the more effective it will be in reducing the residence time of the urea aqueous solution in the concentration section.

Suitably, the volume of the gas flow into the aforementioned gas inlet is adjustable. It will be understood that this can be simply provided by a gas flow connection to a corresponding source of the gas provided with a volume control, such as a gauge.

The foregoing gas flow can, for example, be applied as follows. Generally, a urea production plant (having the sections identified in this description) operated at full capacity, will be guaranteed for a certain maximum level of biuret in the end-product. In the event that the plant is operated at a reduced capacity, the volume flow per time unit of purified urea solution into the concentration section will be reduced. The skilled person, knowing the dimensions and operational parameters of the plant, will be able to easily determine the volume of gas to be added to the purified urea solution in order to compensate for the reduced volume flow. It is also conceivable, irrespective of whether the plant is operated at a reduced capacity, to just reduce the residence time of the purified urea solution in the concentration section, by adding gas to said solution.

In a particularly preferred embodiment of the invention, the added gas is not inert, but comprises ammonia. This reflects a counter-intuitive measure, since a urea plant is normally designed such as to recover ammonia from the urea product, and particularly to prevent ammonia from being vented into the air. Interestingly, however, modern urea plants will comprise one or more acid-scrubbers downstream of urea finishing, which serve to neutralize ammonia before gas streams containing such ammonia are vented into the air. The inventors have realized that the presence of such scrubbers, or of any other available measures that are applied in a urea plant so as to reduce ammonia emissions, in fact make it possible to even add ammonia to the urea stream produced in the plant. By adding the ammonia to the concentration section, the formation of biuret will be further reduced. This is because the formation of biuret from urea, in which ammonia is formed, is a chemical equilibrium. By adding ammonia, the equilibrium will be shifted to the side of the starting material (viz. urea), and accordingly less urea will be converted to biuret. Preferably, the gas consists essentially of ammonia, and more preferably the gas is ammonia. In another embodiment of the invention, the residence time of urea in the concentration section controlled by mechanically varying the effective volume of the concentration section. This can be accomplished, e.g., by providing the evaporation section with a moveable bottom, a moveable wall, or both, allowing to expand or reduce the volume depending on the direction of movement. E.g., in the event of a vertical tube evaporator, a bottom plate can be provided that can move up or down, e.g. by means of protrusions extending into corresponding vertical rails provided in the tube wall. Alternatively, the concentration section is provided, in its internal volume, with an inflatable device, such as a rubber balloon or a bellows, that can be expanded so as to effectively reduce the remaining internal volume of the concentration section.

It will be understood that any of the foregoing embodiments, as well as alternative embodiments, can be combined. In such event, the provision to the plant allowing the residence time of the urea purified solution in the concentration section to be independently controlled, comprises a combination of technical measures.

The invention, in all its embodiments, can be realized in any type of urea plant. Such plants are known to the skilled person. Reference is made to Ullmann's Encyclopedia of Industrial Chemistry, 2010, A27, pages 333-350 on urea.

Preferably, the invention pertains to a process for the preparation of urea according to a stripping process, as conducted in a urea stripping plant.

In a urea stripping plant the decomposition of the ammonium carbamate that has not been converted into urea and the expulsion of the usual ammonia excess largely takes place at a pressure that is essentially almost equal to the pressure in the synthesis reactor. This decomposition and expulsion take place in one or more stripper(s) installed downstream of the reactor, possibly with the aid of a stripping gas such as, for example, carbon dioxide and/or ammonia, and with the addition of heat. It is also possible to apply thermal stripping. Thermal stripping means that use is made exclusively of the supply of heat to decompose ammonium carbamate and remove the ammonia and carbon dioxide present from the urea solution. The gas stream leaving a stripper contains ammonia and carbon dioxide which are condensed in a high-pressure condenser and then returned to the urea synthesis zone.

In a urea stripping plant the synthesis zone is operated at a temperature of 160-240° C. and preferably at a temperature of 170-220° C. The pressure in the synthesis reactor is 12-21 MPa, preferably 12.5-20 MPa, more preferably 13-16 MPa. In the art, these ranges are generally considered to represent "high pressure" (as also used in connection with a conventional "High Pressure Carbamate Condenser"). The gross ammonia to carbon dioxide molar ratio (gross N/C ratio) in the urea synthesis zone of a stripping plant usually is in between 2.2 and 5 and preferably between 2.5 and 4.5 mol/mol. For completeness' sake, it is noted that the synthesis zone will usually operate on the basis of both an external feed of the starting materials, ammonia and carbon dioxide, and recycled starting materials, generally comprising recycled ammonia and carbon dioxide in a free form as well as in the form of ammonium carbamate and/or biuret. The gross N/C ratio, which is a term having a customary meaning in the art, refers to a hypothetical mixture in which all starting materials are converted into free ammonia and carbon dioxide.

The synthesis zone can comprise a single reactor or a plurality of reactors, arranged in parallel or in series. In addition to one or more reactors, the synthesis section comprises a stripper, a condenser and a scrubber, all operating at substantially the same pressure. The synthesis zone is generally referred to as a High Pressure (HP) section.

In the synthesis section the urea solution leaving the urea reactor is fed to a stripper in which a large amount of non-converted ammonia and carbon dioxide is separated from the aqueous urea solution. Such a stripper can be a shell and tube heat exchanger in which the urea solution is fed to the top part at the tube side and a carbon dioxide feed to the synthesis is added to the bottom part of the stripper. At the shell side, high pressure (HP) steam is added to heat the solution via indirect heat exchange. The urea solution leaves the heat exchanger at the bottom part, while the vapor phase leaves the stripper at the top part. The vapor leaving said stripper contains ammonia, carbon dioxide and a small amount of water. Said vapor is condensed in a falling film type heat exchanger or a submerged type of condenser that can be a horizontal type or a vertical type. A horizontal type submerged heat exchanger is described in the aforementioned Ullmann's Encyclopedia of Industrial Chemistry, Vol. A27, 1996, pp 333-350.

After the stripping treatment, the pressure of the stripped urea solution is reduced in a urea recovery section. In the recovery section the non-converted ammonia and carbon dioxide in the urea solution are separated from the urea and water solution. A recovery section comprises usually a heater, a liquid/gas separation section and a condenser. The urea solution entering a recovery section is heated to vaporize the volatile components ammonia and carbon dioxide as well as water from that solution. The heating agent used in the heater is usually steam. The ammonium carbamate aqueous solution formed in a low pressure carbamate condenser in the recovery section, operated at a lower pressure than the pressure in the synthesis section, is preferably returned to the urea synthesis section operating at synthesis pressure. The recovery section is generally a single section or can be a plurality of recovery sections arranged in parallel or in series. The recovery section comprises a heater, a liquid/gas separator and a condenser. The pressure in this recovery section is generally between 200 to 600 kPa. This section is generally referred to as a low pressure (LP) recovery section (or recirculation section, the terms "recovery section" and "recirculation section" in this description are used interchangeably). In the heater of the recovery section the bulk of ammonia and carbon dioxide is separated from the urea and water phase by heating the urea solution. Usually low pressure (LP) steam is used as heating agent. The urea and water phase contains a small amount of dissolved ammonia and carbon dioxide that leaves the recovery section and is sent to a downstream urea processing section where the urea solution is concentrated by evaporating the water from said solution. This section, i.e., the concentration section, is frequently referred to as the evaporation section and it is typically comprised of one or two evaporators, whose vapors are condensed downstream and recycled back to the process.

In some embodiments, in addition to the HP synthesis section and the LP recovery section, a medium pressure (MP) treatment section is present. E.g., WO 02/090323 discloses a urea process and plant of the carbon dioxide stripping type, wherein a MP treatment section is present parallel with the HP stripping section. A similar disclosure is found in EP 2 086 928.

Processes also exist in which a MP treatment section is present in series, downstream of the urea synthesis section. In this respect reference can be made to, e.g., GB 1 542 371, and other disclosures of the Snamprogetti Ammonia and Self-Stripping processes.

In sum, the invention provides a novel method of controlling the formation of biuret in urea production. This is accomplished by reducing or preventing the formation of biuret in a concentration section, particularly in one or more concentrators or evaporators. The method comprises controlling the residence time of a urea aqueous stream treated in such concentration section in a manner independently of the volume flow per time interval of said stream into said concentration section. The residence time can be controlled, e.g., by providing the concentration section with an adjustable volume or by adding a gas to the urea stream to be treated. A combination of such measures can also be applied.

Where in this description, the component parts of a urea plant are discussed, including units, zones, and sections of such a plant, the skilled person will understand how to conduct a urea production process therewith. I.e., also if not explicitly stated, the skilled person will understand the mutual arrangement of such parts. For instance, the skilled person will understand the following: A urea production plant generally comprises fluid connections and lines for process streams (urea production streams), generally including a recirculation circuit. This serves to synthesize and obtain urea, and to make optimal use of reactants by recirculation of unreacted ammonia and carbon dioxide. A urea plant generally also comprises utility connections and lines, generally including a steam circuit. This serves to provide heat where needed in the plant, and to make optimal use of available energy by circulating steam obtained in one part of the plant to another part where heat exchange from such steam can be benefited from. Thereby, also if not explicitly indicated, the person skilled in urea production will normally be able to tell which are liquid streams and which are gas streams, and through which ducts, pipes, or flow lines these are transported and/or recirculated in the plant.

Where, in this description, it is spoken of "fluid communication", this refers to any connection between a first part or section of a plant and a second part or section of a plant via which fluids, i.e., gases, liquids, or supercritical fluids, and more particularly liquids, can flow from the first part of the plant to the second part of the plant. Such fluid communication is typically provided by piping systems, hoses, or other devices well-known to the skilled person for the transportation of fluids.

Where in this description it is spoken of "gas flow connection" this refers to any connection between a first part or section of a plant and a second part or section of a plant via which gas or vapors, notably aqueous vapors, can flow from the first part of the plant to the second part of the plant. Such gas flow lines typically comprise piping systems, or other devices well-known to the skilled person for the transportation of gases, if needed under above or below (vacuum) atmospheric pressures.

The invention claimed is:
1. A process for producing urea, the process comprising
   a. subjecting ammonia and carbon dioxide to urea forming conditions in a urea synthesis section, thereby producing a urea aqueous stream;
   b. sending the urea aqueous stream to a recovery section;
   c. subjecting, in the recovery section, the urea aqueous stream to recovery of unreacted ammonia and carbon dioxide from said urea aqueous stream, thereby producing recovered ammonia and carbon dioxide, and a purified urea aqueous stream;
   d. recycling said recovered ammonia and carbon dioxide to the synthesis section;
   e. sending the purified urea aqueous stream to a concentration section;
   f. subjecting, in the concentration section, the purified urea aqueous stream to removal of water, thereby producing a concentrated urea stream;
   wherein the residence time of the purified urea aqueous stream in the concentration section is controlled inde- pendently of the volume flow per time interval of the purified urea aqueous stream into the concentration section.

2. The process of claim 1, wherein the purified urea aqueous stream is combined with a gas at or before entry into the concentration section.

3. The process of claim 2, wherein the amount of the gas added is greater than any amount of the gas that is soluble in the purified urea aqueous stream.

4. The process of claim 3, wherein the gas is selected from the group consisting of air, nitrogen, and mixtures thereof.

5. The process of claim 2, wherein the gas comprises ammonia.

6. The process of claim 5, wherein the gas consists essentially of ammonia.

7. The process of claim 1, wherein the concentrated urea stream has a concentration of more than 90 wt.

8. The process of claim 3, wherein the gas is substantially insoluble in the purified urea aqueous stream.

9. The process of claim 7, wherein the concentrated urea stream has a concentration of more than 95 wt. %.

\* \* \* \* \*